United States Patent [19]

Takasawa et al.

[11] Patent Number: 4,472,501
[45] Date of Patent: Sep. 18, 1984

[54] PROCESS FOR MANUFACTURING ALCOHOL BY FERMENTATION

[75] Inventors: Seigo Takasawa, Hadano; Yasushi Morikawa, Yokohama; Kenichiro Takayama, Atsugi; Izumi Masunaga, Kawasaki, all of Japan

[73] Assignee: Kyowa Hakko Kogyo Co., Ltd., Tokyo, Japan

[21] Appl. No.: 406,987

[22] Filed: Aug. 10, 1982

[30] Foreign Application Priority Data

Aug. 12, 1981 [JP] Japan .................................. 56-125254

[51] Int. Cl.³ .......................... C12P 7/06; C12P 7/10; C12R 1/645
[52] U.S. Cl. .................................. 435/165; 435/161; 435/163; 435/182; 435/911
[58] Field of Search .................. 426/11; 435/161, 162, 435/163, 164, 165, 171, 174, 182, 911, 924

[56] References Cited

U.S. PATENT DOCUMENTS 3,619,369 11/1971 Onishi ................................ 435/924
4,220,721 9/1980 Emert et al. ........................ 435/163
4,350,765 9/1982 Chibata et al. ..................... 435/161
4,355,108 10/1982 Gaddy et al. ......................... 426/11
4,368,268 1/1983 Gong ................................... 435/163

FOREIGN PATENT DOCUMENTS 0038723 10/1981 European Pat. Off. .
WO81/03032 10/1981 PCT Int'L Appl. .
2075546 11/1981 United Kingdom .

Primary Examiner—Alvin E. Tanenholtz
Assistant Examiner—Marianne S. Minnick
Attorney, Agent, or Firm—Fitzpatrick, Cella, Harper & Scinto

[57] ABSTRACT

Ethanol is produced by culturing the microorganism *Kluyveromyces cellobiovorus* or *Kloeckera apiculata* in a medium containing, as a carbon source, an assimilable source of xylose, cellobiose or both. The carbon source may be provided in the form of hydrolysates of cellulose containing substances such as cotton, wood, straw or paper which are obtained by acid hydrolysis or enzymatic action. At the completion of culturing, ethanol is removed from the culture in a conventional manner.

9 Claims, No Drawings

PROCESS FOR MANUFACTURING ALCOHOL BY FERMENTATION

FIELD OF THE INVENTION

The present invention relates to a process for producing alcohol by fermentation. More specifically, it relates to a process for producing alcohol by fermentation, characterized by culturing a yeast belonging to the genus Kluyveromyces, Candida or Kloeckera and capable of assimilating xylose and/or cellobiose to produce alcohol.

BACKGROUND OF THE INVENTION

Heretofore, in the production of alcohol by fermentation using cellulose as a carbon source, the enzyme or acid hydrolyzate of cellulose has been used and a yeast belonging to the genus Saccharomyces has been mainly used as a seed strain. In such process, pentose (mainly xylose) derived from hemicellulose which is contained in cellulose at the rate of 10–30% is not utilized and the yield of alcohol is rather low. Therefore, cellulose is separated to α-cellulose and hemicellulose; glucose obtained from α-cellulose is utilized for the production of alcohol using a yeast of Saccharomyces and pentose obtained from hemicellulose is utilized for the production of yeast protein using a yeast capable of assimilating it as a carbon source.

Further, it has been tried to utilize the substance obtained by saccharification of cellulose with cellulase. However, cellobiose obtained by the saccharification cannot be converted to alcohol by yeasts of Saccharomyces.

As a result of studies for utilizing xylose and cellobiose which are unutilized resources, the present inventors have found a yeast capable of assimilating xylose and cellobiose as well as glucose to produce alcohol and have completed the invention.

SUMMARY OF THE INVENTION

According to the present invention, alcohol is produced by fermentation using a microorganism capable of assimilating xylose and cellobiose to produce alcohol. As used herein, the term alcohol means ethanol.

DESCRIPTION OF THE INVENTION

As a microorganism used in the present invention, any strain may be used so long as it belongs to the genus Kluyveromyces, Candida or Kloeckera and has both an ability to assimilate xylose and/or cellobiose and an ability to produce alcohol.

Examples of preferred strain include *Candida tropicalis* ATCC 20175, *Candida guilliermondii* ATCC 20118, *Kloeckera apiculata* IAM 4018, NRRL Y-12510 and *Kluyveromyces cellobiovorus* TM 193, NRRL Y-12509.

*Kluyveromyces cellobiovorus* TM 193 and *Kloeckera apiculata* IAM 4018 have been deposited on July 13, 1981 with the culture collection of Agricultural Research Culture Collection (NRRL), 1815, N. University Street, Peoria, Ill. 61604 U.S.A. and are available to the public under culture Nos. NRRL Y-12509 and NRRL Y-12510, respectively.

*Candida tropicalis* ATCC 20175 and *Candida guilliermondii* ATCC 20118 are described in ATCC Catalogue of Strains I 13th edition (1978).

Table 1 shows the assimilability and fermentability of sugar of these strains.

TABLE 1

| Strain | Xylose A* | Xylose F** | Cellobiose A | Cellobiose F | Glucose A | Glucose F |
|---|---|---|---|---|---|---|
| *Kluyveromyces cellobiovorus* TM 193 | + | + | + | + | + | + |
| *Candida tropicalis* ATCC 20175 | + | + | − | − | + | + |
| *Candida guilliermondii* ATCC 20118 | + | + | + | − | + | + |
| *Kloeckera apiculata* IAM 4018 | − | − | + | + | + | + |

*A: Assimilability
**F: Fermentability

Microbiological properties of *Candida tropicalis*, *Candida guilliermondii* and *Kloeckera apiculata* are described in "The Yeast" by Lodder, et al. 1970 edition, pp. 1059, 969 and 1150.

*Kluyveromyces cellobiovorus* TM 193 is a strain isolated and identified by the present inventors and the microbiological properties thereof are shown below.

(a) Growth on various media (1) Observation in yeast extract-malt extract liquid medium After 3 days of culturing at 25° C., the cells are spheroidal to ellipsoidal (2–5)×(3–10)μ. A sediment is present and a ring is formed on the surface. One to four reniform ascospores and a pseudomycelium are formed.

(2) Observation on yeast extract-malt extract agar medium

After 3 days of culturing at 25° C., the cells have the same appearance as above. The culture is cream with pale brown, smooth to somewhat crispulate, dull and flat to somewhat raised. The margin is entire.

(3) Slide Dalman plate culture on potato agar: Pseudomycelium is formed.

(b) Formation of ascospores

One to four reniform ascospores are formed on yeast extract-malt extract agar medium.

(c) Physiological properties (1) Optimum temperature for growth: 15°–30° C.
(2) Optimum pH for growth: 3.0–7.5
(3) Growth on the medium containing potassium nitrate as a sole nitrogen source: −
(4) Growth on the medium containing ethylamine as a sole nitrogen source: +
(5) Liquefaction of gelatin: −
(6) Osmophily: positive in 12% NaCl
(7) Production of carotinoide: −
(8) Splitting of arbutin: +
(9) Requirement for vitamine: +
(10) Cycloheximide resistance: −

(d) Fermentability and assimilability of carbon compounds (1) Fermentability of sugar

| | |
|---|---|
| D-Glucose | + |
| Sucrose | + |
| Cellobiose | + |
| Soluble starch | − |
| D-Galactose | + |
| Lactose | + |

| -continued | |
|---|---|
| Trehalose | − |
| Maltose | − |
| Melibiose | − |
| Raffinose | − |

(2) Assimilability of sole carbon source

| | |
|---|---|
| D-Xylose | + |
| D-Glucose | + |
| D-Galactose | + |
| Maltose | + |
| Sucrose | + |
| Lactose | + |
| Melibiose | − |
| Cellobiose | + |
| Trehalose | + |
| Raffinose | − |
| Melezitose | − |
| Soluble starch | − |
| Ethanol | + |
| Inositol | − |
| D-Mannitol | + |
| Dulcitol | − |

The strain is classified as belonging to the genus Kluyveromyces according to The Yeast edited by J. Lodder, et al. (1970) based on the following properties: vegetative reproduction by multilateral budding, cells spheroidal to ellipsoidal, a mycelium is not formed and reniform ascospores are formed. However, there is no species to which the strain is assigned. The strain is closely related to *Kluyveromyces lactis*, but differs from the species in fermentation of cellobiose, assimilation of melezitose and cycloheximide resistance. Therefore, the strain is identified as a new species of the genus Kluyveromyces and named *Kluyveromyces cellobiovorus nov. sp.*

Any of synthetic medium and natural medium may be used as the medium for the present invention, so long as it properly contains a carbon source, nitrogen source, inorganic materials, and other necessary nutrients.

As the carbon source, at least xylose and/or cellobiose is used and any other carbon source which the microorganism used can assimilate, such as glucose, fructose, galactose, sucrose, maltose, lactose, sorbitol, mannitol, glycerol, starch, starch hydrolyzate, molasses, blackstrap molasses, etc., hydrocarbons such as n-paraffins, kerosene, etc., organic acids such as acetic acid, fumaric acid, lactic acid, pyruvic acid, succinic acid, etc., and alcohols such as methanol, ethanol, etc. may be used.

In the present process, any substance containing xylose and/or cellobiose may be used as well as pure form of xylose and/or cellobiose. Examples of substance containing xylose and/or cellobiose include saccharified substance or hydrolyzates of substance containing α-cellulose and/or hemicellulose such as agricultural products and waste matters thereof such as cotton, wood, rice straw, bagasse, wheat straw and corn stover, and city and industrial wastes such as old newspaper, waste papers, corrugated cardboard and old magazine.

For the saccharification and hydrolysis, enzymatic treatment, hydrolysis of acids such as sulfuric acid, hydrochloric acid, and nitric acid and other physical or chemical treatment may be applied. As the nitrogen source, ammonia, inorganic and organic ammonium salts such as ammonium chloride, ammonium sulfate, ammonium phosphate, ammonium acetate, etc., urea, amines, other nitrogen-containing compounds and peptone, meat extract, yeast extract, corn steep liquor, casein hydrolyzate, fish meal, digest of fish meal, defatted soybeans, digest of defatted soybeans, soybean protein acid-hydrolyzate, various microbial cells, digest of microbial cells, etc. may be used. As the inorganic materials, potassium dihydrogen phosphate, dipotassium hydrogen phosphate, magnesium sulfate, sodium chloride, ferrous sulfate, manganese sulfate, calcium carbonate, etc. are used.

As the other nutrients, vitamines such as thiamine hydrochloride, p-aminobenzoic acid, folic acid, riboflavin, biotin and inositol may be used.

Culturing is carried out at the similar pH, temperature and stirring condition as in the usual production of alcohol using yeast.

The production of alcohol according to the present invention can be carried out using immobilized microbial cells by applying the known method. Examples of carrier in a gel include agar, sodium alginate, polyacrylamide and carrageenan.

A method using calcium alginate gel is described in Enzyme Microb. Technol, Vol. 1, 183–188 (1979) and a method using carrageenan is described in Japanese Published Unexamined Patent Application No. 165796/80. The production of alcohol using immobilized yeast may be carried out by either batch system or continuous column system.

The recovery of alcohol is carried out according to the usual manner.

According to the present invention, alcohol is produced by using xylose or cellobiose as a carbon source. Therefore, substance containing cellulose and hemicellulose which produce xylose or cellobiose by saccharification or hydrolysis may be used. Saccharification of cellulase is usually inhibited by glucose and cellobiose derived from cellulose by hydrolysis with cellulase. If alcohol-producing yeast is added to the saccharification system, glucose derived from cellulose is consumed by the yeast and the inhibition described above is obviated. The simultaneous saccharification and fermentation are carried out according to the method described in U.S. Pat. No. 3,990,944 or U.S. Pat. No. 4,009,075.

The yeast used in examples of the present invention can assimilate glucose and cellobiose. Therefore, the rate of inhibition is very low and reaction proceeds effectively.

Certain specific embodiments of the invention are illustrated by the following representative examples.

EXAMPLE 1

In this example, *Kloeckera apiculata* IAM 4018, *Kluyveromyces cellobiovorus* TM 193 and *Candida guilliermondii* ATCC 20118 are activated on an yeast extract—malt extract agar medium. The activated strains are inoculated into 10 ml of a medium containing 60 g/l cellobiose, 4.5 g/l yeast extract and 7.5 g/l peptone and adjusted to pH 5.5 in a 20 ml-test tube (inside diameter: 14 mm) and incubated at 28° C. for 48 hours. The amounts of microbial cells and alcohol produced are shown in Table 2.

An alcohol-producing yeast, *Saccharomyces cerevisiae* ATCC 20197 which is used as a control does not grow on the above medium.

TABLE 2

| Strain | Amount of microbial cells (g/l) | Yield of alcohol (g/l) |
| --- | --- | --- |
| Kloeckera apiculata IAM 4018 | 5.2 | 6.2 |
| Kluyveromyces cellobiovorus TM 193 | 13.5 | 17.8 |
| Candida guilliermondii ATCC 20118 | 11.8 | trace |

EXAMPLE 2

In this example, *Kluyveromyces cellobiovorus* TM 193, *Candida guilliermondii* ATCC 20118 and *Candida tropicalis* ATCC 20175 are used as the seed strains.

The same procedures as in Example 1 are repeated except that xylose is used instead of cellobiose and the result is shown in Table 3.

*Saccharomyces cerevisiae* ATCC 20197 used as a control does not grow.

TABLE 3

| Strain | Amount of microbial cells (g/l) | Yield of alcohol (g/l) |
| --- | --- | --- |
| Kluyveromyces cellobiovorus TM 193 | 5.2 | 16.5 |
| Candida guilliermondii ATCC 20118 | 12.3 | 3.0 |
| Candida tropicalis ATCC 20175 | 3.9 | 4.3 |

EXAMPLE 3

In this example, *Kluyveromyces cellobiovorus* TM 193, *Saccharomyces cerevisiae* ATCC 20197 and *Candida tropicalis* ATCC 20175 activated in the same manner as in Example 1 are inoculated into a 300 ml-Erlenmeyer flask containing 100 ml of a medium (pH 5.5) comprising 20 g/l glucose, 16 g/l xylose, 5 g/l cellobiose, 4.5 g/l yeast extract and 7.5 g/l peptone and are cultured at 28° C. for 64 hours. The results are shown in Table 4.

The yields of alcohol by the strains *Kluyveromyces cellobiovorus* and *Candida tropicalis* cultured for 64 hours are respectively 1.48 times and 1.12 times that by *Saccharomyces cerevisiae* used as a control.

TABLE 4

| Strain | Amount of microbial cells (g/l) | Yield of alcohol (g/l) | Amount of remaining sugar** (g/l) G | X | C |
| --- | --- | --- | --- | --- | --- |
| Kluyveromyces cellobiovorus | 7.3 | 12.1 | n.d. | n.d. | 1.0 |
| Candida tropicalis | 13.2 | 9.2 | n.d. | n.d. | 4.6 |
| Saccharomyces cerevisiae | 5.7 | 6.7* | n.d. | 16.0 | 4.8 |

*Maximum yield of alcohol is 8.2 g/l by 24 hours of culturing. (n.d.: not detected)
**G: glucose, X: xylose, C: cellobiose

EXAMPLE 4

In this example, *Kloeckera apiculata* IAM 4018 activated in the same manner as in Example 1 is inoculated into 80 ml of a medium containing 100 g/l crystalline cellulose (trade name: Abicel pH 301, product of Asahi Chemical Industry Co., Ltd.), 4.5 g/l yeast extract, 7.5 g/l peptone, 0.1 g/l magnesium sulfate, 3 g/l potassium monohydrogen phosphate, 1 g/l sodium dihydrogen phosphate and 10 g/l calcium carbonate and adjusted to pH 5.0 in a 300 ml-Erlenmeyer flask, and cellulase (trade name: Cellulase Onozuka, product of Kinki Yakuruto Co.) is added to the medium so that it will contain 35 unit/ml CMCase.

The mixture is cultured at 28° C. for 6 days with shaking (220 r.p.m.). The yield of alcohol is 22 g/l and no sugar is detected.

The production of alcohol in the yield of 22 g/l means that the production of sugar is 44 g/l.

The same procedures as described above are repeated except that the strain is not inoculated. The yield of sugar is 23 g/l.

EXAMPLE 5

In this example, *Kluyveromyces cellobiovorus* TM 193 and *Saccharomyces cerevisiae* ATCC 20197 activated in the same manner as in Example 1 are used. Cane bagasse treated with alkali is subjected to enzymatic reaction with cellulase to obtain a sugar solution containing 51 g/l glucose, 9 g/l cellobiose, 17 g/l xylose and 14 g/l xylobiose, and 4.5 g/l yeast extract and 7.5 g/l peptone are added thereto to prepare a medium.

The strains are inoculated into the medium and cultured in the similar manner as in Example 1. The results are shown in Table 5. The yield of alcohol by *Kluyveromyces cellobiovorus* is about 30% higher than that by *Saccharomyces cerevisiae*.

TABLE 5

| Strain | yield of alcohol (g/l) | | |
| --- | --- | --- | --- |
| | 20 HR | 30 HR | 72 HR |
| Kluyveromyces cellobiovorus | 21 | 25 | 29 |
| Saccharomyces cerevisiae | 20 | 22 | 21 |

EXAMPLE 6

The same procedures as in Example 5 are repeated except that 3 l of a sugar solution obtained by saccharification of bagasse and containing 72 g/l glucose, 10 g/l cellobiose, 38 g/l xylose and 7 g/l xylobiose in a 5 l-jar fermenter is used.

The yield of alcohol by *Kluyveromyces cellobiovorus* TM 193 is about 35% higher than that by *Saccharomyces cerevisiae*.

EXAMPLE 7

In this example, *Kluyveromyces cellobiovorus* TM 193 is cultured in the similar manner as in Example 3 for 48 hours. 10 g of the obtained microbial cells is suspended in 100 ml of 2% sodium alginate and the suspension is added dropwise through a nozzle to 1% aqueous calcium chloride solution. Then, 20 ml of the obtained immobilized microbial cells (diameter: 2-3 mm) is packed into a column having inside diameter of 2.5 cm. The same sugar solution as in Example 6 is passed through the column from the bottom thereof at the rate of 10 ml/HR at 30° C.

The concentration of alcohol in flooding solution increases gradually and reaches 47 g/l after four days of reaction. The production is continued in the same yield for one month or more.

The same procedures as described above are repeated except that *Saccharomyces cerevisiae* ATCC 20197 is used. The concentration of alcohol is less than 32 g/l.

What is claimed is:

1. A process for producing ethanol which comprises culturing a microorganism selected from the group consisting of a microorganism having the identifying characteristics of *Kluyveromyces cellobiovorus* NRRL Y-12509 and a microorganism having the identifying characteristics of *Kloeckera apiculata* NRRL Y-12510 and which is capable of producing ethanol and assimilating at least one carbon source selected from the group consisting of xylose and cellobiose, in a medium containing an assimilable source of at least one of said xylose and cellobiose until a recoverable amount of ethanol is produced in the culture liquor and thereafter recovering said ethanol therefrom.

2. A process according to claim 1 wherein said microorganism is *Kluyveromyces cellobiovorus* NRRL Y-12509.

3. A process according to claim 1 wherein said microorganism is *Kloeckera apiculata* NRRL Y-12510.

4. A process according to claim 1 wherein said assimilable carbon source is a hydrolyzate of a substance containing cellulose or hemicellulose.

5. A process according to claim 4 wherein said cellulose or hemicellulose is derived from a substance selected from the group consisting of cotton, wood rice straw, wheat straw, corn stover or paper.

6. A process according to claim 1 wherein said medium contains cellulose and cellulase to provide said assimilable carbon source.

7. A process according to claim 1 wherein said microorganism is immobilized in a gel.

8. A process according to claim 7 wherein said culturing is continuously carried out.

9. A biologically pure culture of the microorganism *Kluyveromyces cellobiovorus* having the identifying characteristic of NRRL Y-12509 which is capable of assimilating cellobiose and xylose to produce ethanol in recoverable amounts.

* * * * *